(12) United States Patent
Gavai et al.

(10) Patent No.: US 7,358,256 B2
(45) Date of Patent: Apr. 15, 2008

(54) ATP COMPETITIVE KINASE INHIBITORS

(75) Inventors: Ashvinikumar V. Gavai, Princeton Junction, NJ (US); Ping Chen, Belle Mead, NJ (US); Yufen Zhao, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 24 days.

(21) Appl. No.: 11/389,797

(22) Filed: Mar. 27, 2006

(65) Prior Publication Data

US 2006/0217369 A1 Sep. 28, 2006

Related U.S. Application Data

(60) Provisional application No. 60/665,826, filed on Mar. 28, 2005.

(51) Int. Cl.
*A61K 31/517* (2006.01)
*C07D 239/72* (2006.01)

(52) U.S. Cl. .................. 514/266.22; 544/293
(58) Field of Classification Search ........... 514/217.05, 514/266.22; 540/600; 544/293
See application file for complete search history.

(56) References Cited

U.S. PATENT DOCUMENTS

| | | | |
|---|---|---|---|
| 5,064,833 A | 11/1991 | Ife et al. | |
| 5,457,105 A | 10/1995 | Barker | |
| 5,580,870 A | 12/1996 | Barker et al. | |
| 5,616,582 A | 4/1997 | Barker | |
| 6,057,326 A * | 5/2000 | Brasca et al. | 514/266.21 |
| 6,972,288 B1 | 12/2005 | Himmelsbach et al. | |
| 2006/0155125 A1* | 7/2006 | Chen et al. | 544/184 |

FOREIGN PATENT DOCUMENTS

| | | |
|---|---|---|
| WO | WO 97/03069 | 1/1997 |
| WO | WO 00/51991 | 9/2000 |
| WO | WO 00/55141 | 9/2000 |

* cited by examiner

*Primary Examiner*—Emily Bernhardt
*Assistant Examiner*—Tamthom N Truong
(74) *Attorney, Agent, or Firm*—Elliott Korsen

(57) ABSTRACT

The present invention provides compounds of formula I

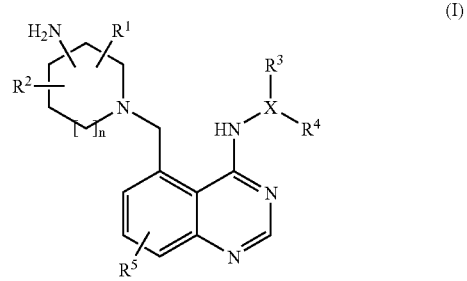

and pharmaceutically acceptable salts thereof.

The formula I compounds inhibit tyrosine kinase activity of growth factor receptors such as HER1, HER2 and HER4 thereby making them useful as antiproliferative agents. The formula I compounds are also useful for the treatment of other diseases associated with signal transduction pathways operating through growth factor receptors.

2 Claims, No Drawings

ATP COMPETITIVE KINASE INHIBITORS

This application claims the benefit of U.S. Provisional Application No. 60/665,826, filed Mar. 28, 2005, incorporated herein by reference in its entirety.

FIELD OF THE INVENTION

This invention relates to compounds that inhibit the tyrosine kinase activity of growth factor receptors such as HER1, HER2, and HER4 thereby making them useful as anti-cancer agents. The compounds are also useful in the treatment of diseases, other than cancer, which are associated with signal transduction pathways operating through growth factor receptors such as HER1, HER2 and HER4.

BACKGROUND OF THE INVENTION

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain.

The human epidermal growth factor receptor (HER) family consists of four distinct receptor tyrosine kinases referred to HER1, HER2, HER3, and HER4. These kinases are also referred to as erbB1, erbB2, etc. HER1 is also commonly referred to as the epidermal growth factor (EGF) receptor. With the exception of HER3, these receptors have intrinsic protein kinase activity that is specific for tyrosine residues of phosphoacceptor proteins. The HER kinases are expressed in most epithelial cells as well as tumor cells of epithelial origin. They are also often expressed in tumor cells of mesenchymal origin such as sarcomas or rhabdomyosarcomas. RTKs such as HER1 and HER2 are involved in cell proliferation and are associated with diseases such as psoriasis and cancer. Disruption of signal transduction by inhibition of these kinases would have an antiproliferative and therapeutic effect.

The enzymatic activity of receptor tyrosine kinases can be stimulated by either overexpression, or by ligand-mediated dimerization. The formation of homodimers as well as heterodimers has been demonstrated for the HER receptor family. An example of homodimerization is the dimerization of HER1 (EGF receptor) by one of the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization as involving HER2 and HER3, or a HER3/HER4 combination, results in a significant stimulation of the tyrosine kinase activity of the receptor dimers even though one of the receptors (HER3) is enzymatically inert. The kinase activity of HER2 has been shown to be activated also by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase) and the phosphatidylinositol 3-kinase (PI3 kinase). Activation of these pathways have been shown to lead to cell proliferation and the inhibition of apoptosis. Inhibition of HER kinase signaling has been shown to inhibit cell proliferation and survival.

Other RTKs such as VEGFR-2 are associated with the proliferation of endothelial cells as well as tumor cells. Disruption of this pathway would have an antiproliferative effect and a therapeutic effect on disorders related to vasculogenesis or angiogenesis.

DETAILED DESCRIPTION OF THE INVENTION

The present invention provides for compounds of formula I, pharmaceutical compositions employing such compounds and for methods of using such compounds.

In accordance with the present invention, there are disclosed compounds of formula I

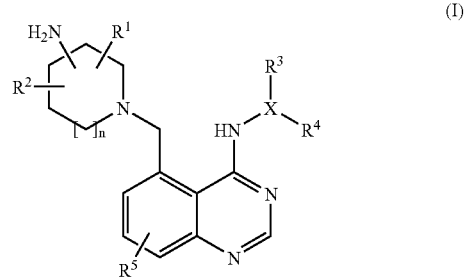

(I)

wherein the symbols have the following meanings and are, for each occurrence, independently selected:

$R^1$ and $R^2$ are independently selected from the group consisting of hydrogen, halogen, —OH, alkyl, substituted alkyl, —CN, —NH$_2$, —CONHR$^3$, —OCONHR$^3$, —CONHSO$_2$R$^3$, —NHCONHR$^3$, —CH$_2$OR$^3$, —CH$_2$CH$_2$OH, alkoxy, substituted alkoxy, aryl, substituted aryl, aryloxy, substituted aryloxy, —CF$_3$ and —OCF$_3$, two of which may be attached to the same ring carbon atom provided that the resultant compound is chemically stable;

$R^3$ is hydrogen or C$_1$-C$_4$ alkyl;

$R^4$ is an optionally substituted aryl or heteroaryl group; said substituents on the substituted aryl or substituted heteroaryl group are selected from the group consisting of one or more hydrogen, halogen, alkyl, substituted alkyl, alkynyl, substituted alkynyl, alkoxy, substituted alkoxy, aryl, substituted aryl, aralkyl, substituted aralkyl, aryloxy and substituted aryloxy;

$R^5$ is halogen, C$_1$-C$_6$ alkyl or C$_1$-C$_6$ alkoxy;

X is a direct bond or —CH—;

n is 0, 1 or 2;

or a pharmaceutically acceptable salt or stereoisomer thereof.

These compounds inhibit the tyrosine kinase activity of growth factor receptors such as HER2.

In another embodiment, the invention comprises a compound of formula II wherein

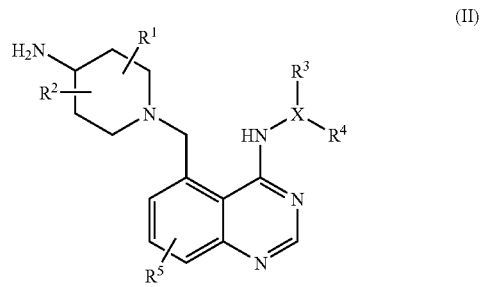

(II)

$R^1$ and $R^2$ are independently selected from the group consisting of hydrogen, halogen, —OH, alkyl, substituted alkyl, —CN, —NH$_2$, —CONHR$^3$, —OCONHR$^3$, —CONHSO$_2$R$^3$, —NHCONHR$^3$, —CH$_2$OR$^3$, —CH$_2$CH$_2$OH, alkoxy, substituted alkoxy, aryl, substituted aryl, aryloxy, substituted aryloxy, —CF$_3$ and —OCF$_3$, two of which may be attached to the same ring carbon atom provided that the resultant compound is chemically stable;

R$^3$ is hydrogen or C$_1$-C$_4$ alkyl;

R$^4$ is an optionally substituted aryl or heteroaryl group; said substituents on the substituted aryl or substituted heteroaryl group are selected from the group consisting of one or more hydrogen, halogen, alkyl, substituted alkyl, alkynyl, substituted alkynyl, alkoxy, substituted alkoxy, aryl, substituted aryl, aralkyl, substituted aralkyl, aryloxy and substituted aryloxy;

R$^5$ is halogen, C$_1$-C$_6$ alkyl or C$_1$-C$_6$ alkoxy;

X is a direct bond or —CH—;

or a pharmaceutically acceptable salt or stereoisomer thereof.

In another embodiment, the invention comprises a compound of formula III,

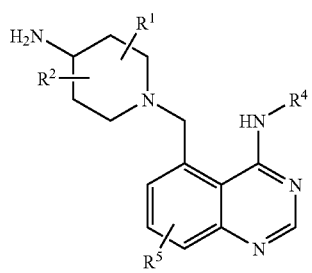

(III)

wherein
R$^1$ and R$^2$ are independently selected from the group consisting of hydrogen, halogen, —OH, alkyl, substituted alkyl, —CN, —NH$_2$, —CONHR$^3$, —OCONHR$^3$, —CONHSO$_2$R$^3$, —NHCONHR$^3$, —CH$_2$OR$^3$, —CH$_2$CH$_2$OH, alkoxy, substituted alkoxy, aryl, substituted aryl, aryloxy, substituted aryloxy, —CF$_3$ and —OCF$_3$ two of which may be attached to the same ring carbon atom provided that the resultant compound is chemically stable;

R$^3$ is hydrogen or C$_1$-C$_4$ alkyl;

R$^4$ is an optionally substituted aryl or heteroaryl group; said substituents on the substituted aryl or substituted heteroaryl group are selected from the group consisting of one or more hydrogen, halogen, alkyl, substituted alkyl, alkynyl, substituted alkynyl, alkoxy, substituted alkoxy, aryl, substituted aryl, aralkyl, substituted aralkyl, aryloxy and substituted aryloxy;

R$^5$ is halogen, C$_1$-C$_6$ alkyl or C$_1$-C$_6$ alkoxy;

or a pharmaceutically acceptable salt or stereoisomer thereof.

In another embodiment, the invention comprises a compound of formula III, wherein
R$^1$ and R$^2$ are independently selected from the group consisting of hydrogen, —CONHR$^3$, —CH$_2$OR$^3$ and OH;

R$^4$ is phenyl substituted with one or more hydrogen, halogen, alkyl, substituted alkyl, alkynyl, substituted alkynyl, alkoxy or substituted alkoxy;

or a pharmaceutically acceptable salt or stereoisomer thereof.

Preferred compounds of the invention include the following (3R,4R)-4-amino-1-((4-(3-methoxyphenylamino) quinazolin-5-yl)methyl)-N-methylpiperidine-3-carboxamide, (3R,4R)-4-amino-1-[[4-[(3-chlorophenyl)amino]-5-quinazolinyl]methyl]-3-piperidinol, (3R,4R)-4-amino-1-[[4-[(3-ethynylphenyl)amino]-5-quinazolinyl]methyl]-3-piperidinol, N-(4-(3-fluorobenzyloxy)-3-chlorophenyl)-5-((4-aminopiperidin-1-yl)methyl)quinazolin-4-amine, (3R,4R)-1-((4-(1-(3-fluorobenzyl)-1H-indazole-5-ylamino) quinazolin-5-yl)methyl)-4-aminopiperidin-3-ol, (3R,4R)-4-amino-1-((4-(3-methoxyphenylamino)quinazolin-5-yl)methyl)-3-piperidinol, 5-[(4-amino-1-piperidinyl)methyl]-N-(3-methoxyphenyl)-4-quinazolinamine, ((3R,4R)-4-amino-1-((4-(3-ethynylphenylamino)quinazolin-5-yl)methyl)piperidin-3-yl)methanol, or a pharmaceutically acceptable salt thereof.

The following are definitions of terms that may be used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. SO2NH2, substituted sulfonamido, nitro, cyano, carboxy, carbamyl, e.g. CONH2, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl or a substituted aryl group bonded directly through an alkyl group, such as benzyl.

The term "aryloxy" refers to an aryl or a substituted aryl group bonded directly through an alkoxy group, such as methoxy or ethoxy.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, oxetanyl, pyrazolyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents.

Also included are smaller heterocyclyls, such as, epoxides and aziridines.

The term "carbocyclic ring" refers to stable, saturated or partially unsaturated monocyclic hydrocarbon rings of 3 to 7 carbon atoms such as cyclopropyl, cyclobutyl, cyclopentyl, cyclohexyl and cycloheptyl. The term "optionally substituted" as it refers to "carbocyclic ring" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Any compound that will be converted in vivo to provide the bioactive agent (i.e., the compound for formulas I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992).

It should further be understood that solvates (e.g., hydrates) of the compounds of formula I are also with the scope of the present invention. Methods of solvation are generally known in the art.

Utility

Compounds such as those described in this invention inhibit the protein tyrosine kinase activity of members of the HER family of receptors. These inhibitors will be useful in the treatment of proliferative diseases that are dependent on signaling by one or more of these receptors. Such diseases include psoriasis, rheumatoid arthritis, and solid tumors of the lung, head and neck, breast, colon, ovary, and prostate. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with HER1 (EGF receptor) and HER2, especially those tumors which are significantly dependent on HER1 or HER2 for their growth and spread, including for example, cancers of the bladder, squamous cell, head, colorectal, oesophageal, gynecological (such as ovarian), pancreas, breast, prostate, vulva, skin, brain, genitourinary tract, lymphatic system (such as thyroid), stomach, larynx and lung. In another embodiment, the compounds of the present invention are also useful in the treatment of noncancerous disorders such as psoriasis and rheumatoid arthritis.

Thus according to a further aspect of the invention there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

By virtue of their ability to inhibit HER1, HER2, and HER4 kinases, compounds of the present invention can be used for the treatment of proliferative diseases, including psoriasis and cancer. The HER1 receptor kinase has been shown to be expressed and activated in many solid tumors including head and neck, prostate, non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor efficacy in preclincal and clinical studies. It is therefore expected that inhibitors of the HER1 and HER2 kinases will have efficacy in the treatment of tumors that depend on signaling from either of the two receptors. In addition, these compounds will have efficacy in inhibiting tumors that rely on HER receptor heterodimer signaling. These compounds are expected to have efficacy either as single agent or in combination (simultaneous or sequentially) with other chemotherapeutic agents such as Taxol®, adriamycin, and cisplatin. Since HER1 and HER2 signaling has been shown to regulate expression of angiogenic factors such as vascular endothelial growth factor (VEGF) and interleukin 8 (IL8), these compounds are expected to have anti-tumor efficacy resulting from the inhibition of angiogenesis in addition to the inhibition of tumor cell proliferation and survival. The HER2 receptor has been shown to be involved in the hyperproliferation of synovial cells in rheumatoid arthritis, and may contribute to the angiogenic component of that inflammatory disease state. The inhibitors described in this invention are therefore expected to have efficacy in the treatment of rheumatoid arthritis. The ability of these compounds to inhibit HER1 further adds to their use as anti-angiogenic agents. See the following documents and references cited therein: Schlessinger J., "Cell signaling by receptor tyrosine kinases", Cell 103(2), p. 211-225 (2000); Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", J. of Clin. Oncol. 17(9), p. 2639-2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904-914 (2000); Satoh, K., Kikuchi, S., Sekimata, M., Kabuyama, Y., Homma, M. K., and Homma Y., "Involvement of ErbB-2 in rheumatoid synovial cell growth", *Arthritis Rheum.* 44(2), p. 260-265 (2001).

The antiproliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlortrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; Her 1 and Her 2 inhibitors including anti-Her2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and BMS-354825; Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; IGF1R inhibitors such as those disclosed in US2004/44203A1, inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*,12R*,16S*]]-3-[2-[2-(aminomethyl)-4-thiazolyl[-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, goserelin acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microbtubule agents such as epothilone analogs, discodermolide analogs, and eleutherobin analogs); topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the present invention are of interest for their antiproliferative effects.

Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, and osteosarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as HER1 (EGF receptor), HER2, or HER4.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

HER1, HER2 or HER4 Kinase Assays

Compounds of interest were assayed in a kinase buffer that contained 20 mM Tris.HCl, pH 7.5, 10 mM $MnCl_2$, 0.5 mM dithiothreitol, bovine serum albumin at 0.1 mg/ml, poly(glu/tyr, 4:1) at 0.1 mg/ml, 1 µM ATP, and 4 µCi/ml [γ-$^{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1 and HER4, the cytoplasmic sequences of the receptors were expressed in insect cells as GST fusion proteins, which were purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

The instant compounds inhibit HER1, HER2, and HER4 kinases with IC50 values between 0.001 to 25 µM. Preferred compounds have $IC_{50}$ values between 0.001-5.0 µM. More preferred compounds have $IC_{50}$ values between 0.001-1.0 µM. Most preferred compounds have $IC_{50}$ values between 0.001-0.1 µM.

Methods of Preparation

Certain compounds of formula I may generally be prepared according to the following schemes and the knowledge of one skilled in the art.

Scheme I

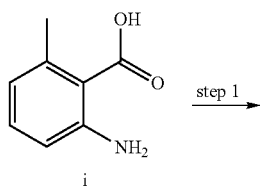

i

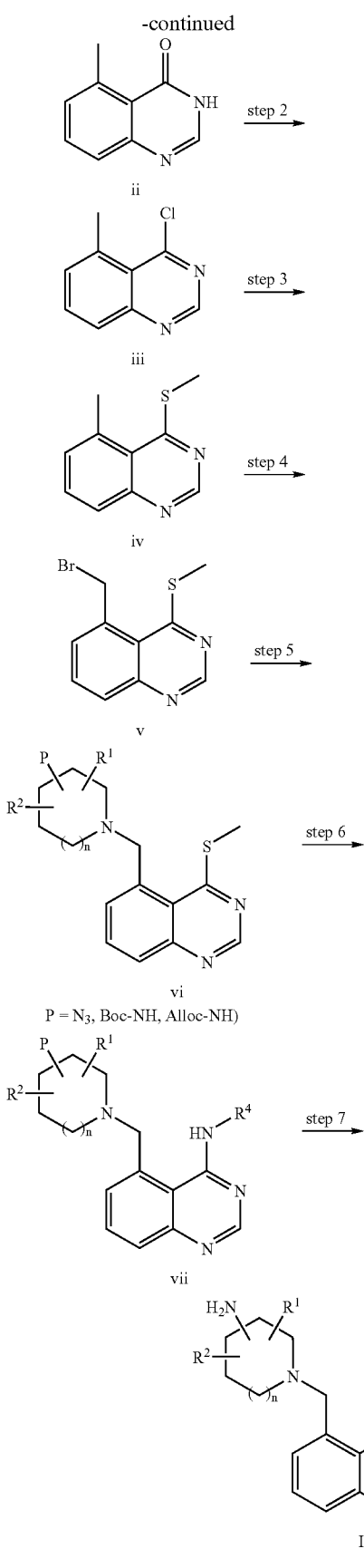

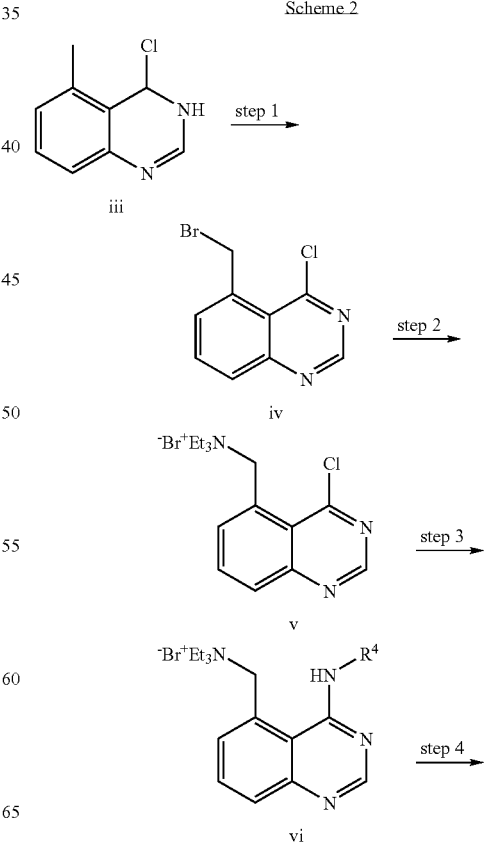

Step 1: Compound ii is obtained by heating Compound i with a reagent such as formaldehyde at reflux or in a microwave oven reactor.

Step 2: Treatment of Compound ii with a chlorinating reagent, such as $POCl_3$, in the presence of a base, such as N,N-diisopropylethylamine, affords Compound iii.

Step 3: Treatment of Compound iii with a reagent such as sodium thiomethoxide affords Compound iv.

Step 4: Halogenation of the $C_5$-methyl group of Compound iv is affected by treatment with a halogenating reagent, such as N-bromosuccinimide. The reaction is preformed under an inert atmosphere, such as argon, and in the presence of a radical initiator, such as dibenzoyl peroxide, or 2,2'-azobisisobutyronitrile to afford Compound v.

Step 5: Treatment of Compound v with an appropriately functionalized primary or secondary amine in the presence of a base such as triethyl amine or diisopropylethyl-amine affords Compound vi.

Step 6: Treatment of Compound vi with $R^4$—$NH_2$ in an aprotic solvent, such as acetonitrile, chloroform or THF, in the presence of a catalyst, such as silver nitrate, or mercury chloride, affords the compound vii.

Step 7: Compound vii can be further converted to compounds of general formula I by: a) reduction (where P=$N_3$), or b) removal of protecting group (where P=Boc-NH or Alloc-NH) using procedures generally known to those skilled in the art.

For Compound vii where $R^1$=ester, it can be further converted to an acid, alcohol, amide, or an acyl sulfonamide functionalities using procedures generally known to those skilled in the art.

Alternatively, compounds of general formula I may be prepared as shown in Scheme 2.

-continued

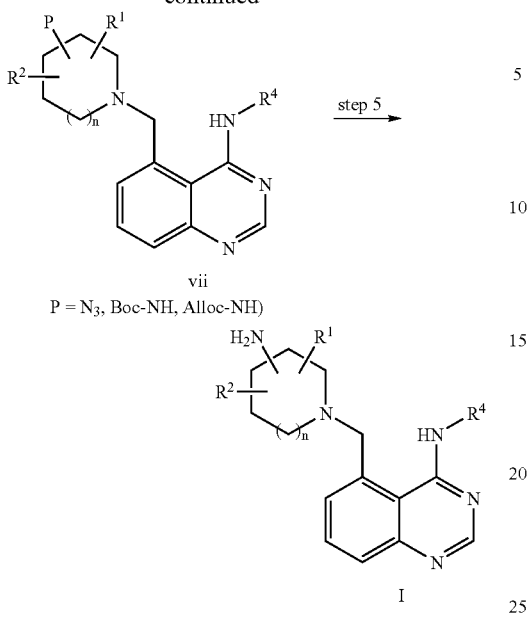

P = N₃, Boc-NH, Alloc-NH)

Step 1: Compound iii can be converted to bromide iv via halogenation of the C₅-methyl group using a halogenating reagent, such as N-bromosuccinimide. The reaction is preformed under an inert atmosphere, such as argon, and in the presence of a radical initiator, such as dibenzoyl peroxide, or 2,2'-azobisisobutyronitrile to afford Compound iv.

Step 2: Compound v, the ammonium salt, can be obtained from Compound iv by treatment with a tertiary base such as triethylamine in an anhydrous solvent such as THF.

Step 3: Treatment of Compound v with $R^4$—NH₂ or its anion form in an aprotic solvent, such as acetonitrile, chloroform or THF, in the presence of a base such as triethyl amine or diisopropylethylamine affords Compound vi.

Step 4: Treatment of Compound vi with with an appropriately functionalized primary or secondary amine in the presence of a base, such as triethyl amine or diisopropylethylamine, affords Compounds vii.

Step 5: Compound vii can be further converted to compounds of general formula I by: a) reduction (where P=N₃), or b) removal of protecting group (where P=Boc-NH or Alloc-NH) using procedures generally known to those skilled in the art.

For Compound vii where $R^1$=ester, it can be further converted to an acid, alcohol, amide, or an acyl sulfonamide functionalities using procedures generally known to those skilled in the art.

In addition, other compounds of formula I may be prepared using procedures generally known to those skilled in the art. In particular, the following examples provide additional methods for the preparation of the compounds of this invention.

The invention will now be further described by the following working examples(s), which are preferred embodiments of the invention. All temperatures are in degrees Celsius (° C.) unless otherwise indicated. "HPLC Ret Time" is the HPLC retention time that was obtained under the following conditions: column type and length, gradient time [unless otherwise indicated, all gradients started with 100% solvent A (10% MeOH, 90% H₂O, 0.1% TFA) and ended with 100% solvent B (90% MeOH, 10% H₂O, 0.1% TFA)], flow rate (mL/min). UV detection was always conducted at 220 nM. These examples are illustrative rather than limiting and it is to be understood that there may be other embodiments that fall within the spirit and scope of the invention as defined by the claims appended hereto.

EXAMPLE 1

(3R,4R)-4-amino-1-((4-(4-fluoro-3-methoxyphenylamino)quinazolin-5-yl)methyl)-3-piperidinol

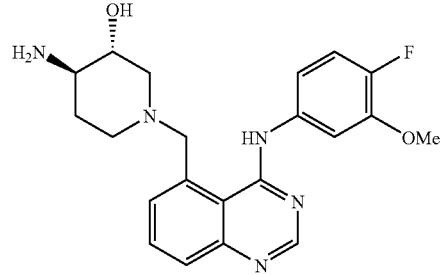

1A. Preparation of 5-methylquinazolin-4(3H)-one

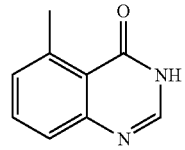

A mixture of 2-amino-6-methylbenzoic acid (5 g, 33 mmol) and formamide (15 ml) was heated in a microwave oven reactor at 180° C. for 30 min. After cooling to room temperature, the solid was collected by filtration, washed with water and dried under vacuum to give 1A (3.89 g, 73%) as a solid. The compound has an analytical HPLC retention time=1.019 min (Chromolith SpeedROD column 4.6×50 mm, 10-90% aqueous methanol containing 0.1% TFA over 4 minutes, 4 mL/min, monitoring at 254 nm) and a LC/MS $M^++H=161^+$.

1B. Preparation of 4-chloro-5-methylquinazoline

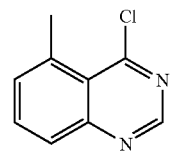

To a solution of 1A (1.44 g, 9.0 mmol) in toluene (24 ml) was added POCl₃ (13.5 ml) and DEA (3.6 ml). The mixture was refluxed under N₂ for 30 min. After cooling to room temperature, the reaction mixture was concentrated under vacuum. The residue was dissolved in EtOAc, washed with 10% citric acid solution, followed by saturated NaHCO₃. The residue was dried with MgSO₄, filtered, and concentrated to give 1B (1.37 g, 85%) as a solid. ¹H-NMR (400 MHz, CDCl₃): 8.96 (s, 1H), 7.94 (d, J=8.52 Hz, 1H), 7.80 (dd, J=7.17 Hz, J=8.52 Hz, 1H), 7.51 (d, J=7.17 Hz, 1H), 3.05 (s, 3H).

1C. Preparation of 5-methyl-4-(methylthio)quinazoline

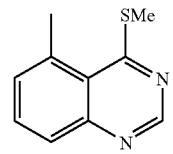

To a suspension of sodium thiomethoxide (0.806 g, 11.5 mmol) in THF (40 ml) at 0° C. was added 1B (1.368 g, 7.66 mmol) in THF (25 ml). The mixture was stirred at room temperature for 1.5 h. The reaction mixture was concentrated to about 15 ml, and water (100 ml) was added. The slurry was stirred at 0° C. for 30 min. The solid was collected by filtration, washed with water and dried to give 1C (1.209 g, 83%) as a solid. The compound has an analytical HPLC retention time=1.899 min (Chromolith SpeedROD column 4.6×50 mm, 10-90% aqueous methanol containing 0.1% TFA over 4 minutes, 4 mL/min, monitoring at 254 nm) and a LC/MS M++H=191+.

1D. Preparation of (3R,4R)-4-azido-1-((4-(methylthio)quinazolin-5-yl)methyl)piperidin-3-ol

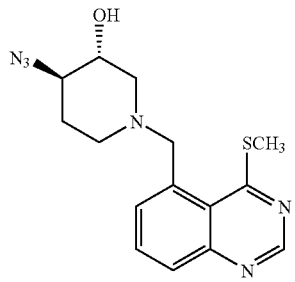

To a mixture of 1C (1.19 g, 6.25 mmol), AIBN (111.2 mg, 0.625 mmol), and NBS (1.129 g, 6.875 mmol) under $N_2$ was added $CCl_4$ (30 ml). The mixture was degassed under vacuum, purged with nitrogen (2×) and heated to 80° C. for 40 min. After cooling to room temperature, the solid was removed by filtration and the filtrate was concentrated under reduced pressure. The residue was dissolved in dichloroethane (30 ml). (3R,4R)-4-azidopiperidin-3-ol (976 mg, 6.875 mmol), (prepared as described in U.S. patent application Ser. No. 11/019,901) and TEA (1.04 ml, 7.5 mmol) were subsequently added. The mixture was stirred at room temperature for 1 h, then at 75° C. for 30 min. After cooling to room temperature, the reaction mixture was washed with saturated $NaHCO_3$, then extracted with 2N HCl (40 ml). The acidic aqueous layer was separated and basified with 50% NaOH. Solid product was collected by filtration, washed with water and dried under high vacuum to give 1D (1.51 g, 73%) as a solid. The compound has an analytical HPLC retention time=1.106 min (Chromolith SpeedROD column 4.6×50 mm, 10-90% aqueous methanol containing 0.1% TFA over 4 minutes, 4 mL/min, monitoring at 254 nm) and a LC/MS M++H=331+.

1E. Preparation of (3R,4R)-4-amino-1-((4-(4-fluoro-3-methoxyphenylamino) quinazolin-5-yl)methyl) piperidin-3-ol

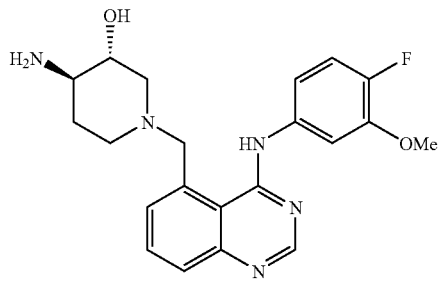

To a suspension mixture of 1D (82.6 mg, 0.25 mmol) and 4-fluoro-3-methoxy-aniline (53 mg, 0.375 mmol) in $CH_3CN$ (3 ml) was added $AgNO_3$ (63.7 mg, 0.375 mmol). The reaction mixture was heated at 70° C. for 30 min. After cooling to room temperature, the solid was removed by filtration through a pad of Celite. The filtrate was concentrated, and the residue was dissolved in EtOAc, washed twice with water. The organic layer was concentrated to give a crude intermediate, which was used without further purification.

The above intermediate was dissolved in a mixture of $THF/H_2O$ (2 ml/0.2 ml) and $PPH_3$ (131 mg, 0.5 mmol) was added. The mixture was heated at 70° C. for 2 h. After cooling to room temperature, the reaction mixture was purified by SCX column (2 g), followed by silica gel flash column (DCM/MeOH/$NH_4OH$=90/10/1) to give 1E (33.0 mg, 33%) as a solid. The compound has an analytical HPLC retention time=1.182 min (Chromolith SpeedROD column 4.6×50 mm, 10-90% aqueous methanol containing 0.1% TFA over 4 minutes, 4 mL/min, monitoring at 254 nm) and a LC/MS M++H=398+.

EXAMPLES 2-13

Compounds 2-13 were prepared using a similar process as the compound in Example 1 utilizing the corresponding chiral 3-hydroxy-4-azidopiperidine and anilines or benzyl amines.

| Ex. | Y | R4—NH | Compound Name | [M + H]+ | HPLC Ret Time (min) |
|---|---|---|---|---|---|
| 2 | 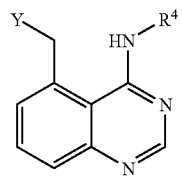 | HN—⌬—Cl | (3R,4R)-4-amino-1-[[4-[(3-chlorophenyl)amino]-5-quinazolinyl]methyl]-3-piperidinol | 384 | 1.417 |

-continued

| Ex. | Y | R⁴—NH | Compound Name | [M + H]⁺ | HPLC Ret Time (min) |
|---|---|---|---|---|---|
| 3 | (3R,4R) 4-amino-3-hydroxy-1-methylpiperidine | 3-ethynylphenyl-NH(Me) | (3R,4R)-4-amino-1-[[4-[(3-ethynylphenyl)amino]-5-quinazolinyl]methyl]-3-piperidinol | 374 | 1.356 |
| 4 | (3R,4R) 4-amino-3-hydroxy-1-methylpiperidine | 3-chloro-4-fluorophenyl-NH(Me) | (3R,4R)-4-amino-1-[[4-[(3-chloro-4-fluorophenyl)amino]-5-quinazolinyl]methyl]-3-piperidinol | 402 | 1.452 |
| 5 | (3R,4R) 4-amino-3-hydroxy-1-methylpiperidine | 3-methylphenyl-NH(Me) | (3R,4R)-4-amino-1-[[4-[(3-methylphenyl)amino]-5-quinazolinyl]methyl]-3-piperidinol | 364 | 1.337 |
| 6 | (3R,4R) 4-amino-3-hydroxy-1-methylpiperidine | 2-methyl-1H-pyrrolo[2,3-b]pyridin-5-yl-NH(Me) | (3R,4R)-4-amino-1-[[4-[(2-methyl-1H-pyrrolo[2,3-b]pyridin-5-yl)amino]-5-quinazolinyl]methyl]-3-piperidinol | 404 | 1.200 |
| 7 | (3R,4R) 4-amino-3-hydroxy-1-methylpiperidine | (1R)-1-phenylethyl-NH(Me) | (3R,4R)-4-amino-1-[[4-[[(1R)-1-phenylethyl]amino]-5-quinazolinyl]methyl]-3-piperidinol | 378 | 1.550 |
| 8 | (3R,4R) 4-amino-3-hydroxy-1-methylpiperidine | (1S)-1-phenylethyl-NH(Me) | (3R,4R)-4-amino-1-[[4-[[(1S)-1-phenylethyl]amino]-5-quinazolinyl]methyl]-3-piperidinol | 378 | 1.600 |
| 9 | (3R,4S) 4-amino-3-hydroxy-1-methylpiperidine | 3-methoxyphenyl-NH(Me) | (3R,4S)-4-amino-1-[[4-[(3-methoxyphenyl)amino]-5-quinazolinyl]methyl]-3-piperidinol | 380 | 1.228 |
| 10 | (3R,4S) 4-amino-3-hydroxy-1-methylpiperidine | 3-ethynylphenyl-NH(Me) | (3R,4S)-4-amino-1-[[4-[(3-ethynylphenyl)amino]-5-quinazolinyl]methyl]-3-piperidinol | 374 | 1.324 |

-continued

| Ex. | Y | R⁴—NH | Compound Name | [M + H]⁺ | HPLC Ret Time (min) |
|---|---|---|---|---|---|
| 11 | (3S,4R)-4-amino-3-hydroxy-1-methylpiperidine, Y=OH | 3-methoxyphenylamino | (3S,4R)-4-amino-1-[[4-[(3-methoxyphenyl)amino]-5-quinazolinyl]methyl]-3-piperidinol | 380 | 1.255 |
| 12 | (3S,4R)-4-amino-3-hydroxy-1-methylpiperidine, Y=OH | 3-ethynylphenylamino | (3S,4R)-4-amino-1-[[4-[(3-ethynylphenyl)amino]-5-quinazolinyl]methyl]-3-piperidinol | 374 | 1.369 |
| 13 | (3S,4R)-4-amino-3-hydroxy-1-methylpiperidine, Y=OH | 3-chloro-4-fluorophenylamino | (3S,4R)-4-amino-1-[[4-[(3-chloro-4-fluorophenyl)amino]-5-quinazolinyl]methyl]-3-piperidinol | 402 | 1.476 |

EXAMPLES 14

5-((4-aminopiperidin-1-yl)methyl)-N-(3-methoxyphenyl)quinazolin-4-amine

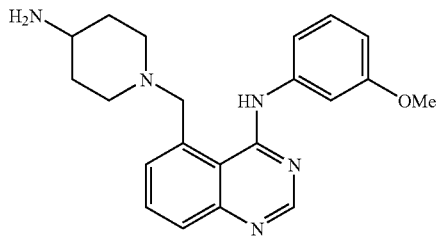

14A. Preparation of N-((4-chloroquinazolin-5-yl)methyl)-N,N-diethylethanaminium bromide

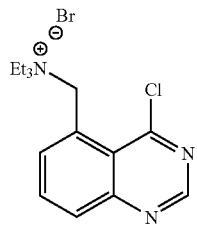

To a mixture of 1B (373 mg, 2.09 mmol), 2,2'-azobisisobutyronitrile (37.2 mg, 0.209 mmol) and N-bromosuccinimide (395 mg, 2.40 mmol) under N₂ was added CCl₄ (10 ml). The mixture was degassed under vacuum, purged twice with N₂, and heated to 80° C. for 1 h. The mixture was allowed to cool to room temperature and the solid was removed by filtration. The filtrate was washed with cold, dilute sodium bicarbonate solution and cold brine, dried over sodium sulfate and concentrated under vacuum. The resulting solid was dissolved in THF (3 ml) and triethylamine (0.7 ml) was added. The mixture was allowed to stir at room temeperature overnight. The newly formed solid was collected by filtration, washed with THF and diethyl ether, dried under a flow of nitrogen, then under high vaccum to give 14A (323 mg, 43%) as a solid. ¹H-NMR (400 MHz, DMSO-d₆): 8.47 (s, 1H), 7.94 (m, 2H), 7.64 (dd, J₁=6.8 Hz, J₂=0.8 Hz, 1H), 5.38 (s, 2H), 3.07 (q, J=7.2 Hz, 6H), 1.27 (t, J=7.2 Hz, 9H).

14B. Preparation of 5-((4-aminopiperidin-1-yl)methyl)-N-(3-methoxyphenyl) quinazolin-4-amine

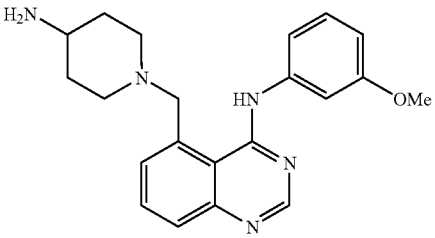

A mixture of 14A (80 mg, 0.223 mmol) and 3-methoxyaniline (18.6 mg, 0.151 mmol) in CH₃CN (1.5 ml) was heated at 55° C. for 2 h. After cooling to room temperature, 4-N-Boc-aminopiperidine (300 mg, 1.5 mmol) was added and the mixture was heated at 60° C. overnight. The reaction mixture was concentrated in vacuo and the residue was purified by prep HPLC. The desired fraction was concentrated and the resulting residue was dissolved in a mixture of TFA/DCM (1 ml/1 ml) and stirred at room temperature for 1 h, then concentrated. The residue was purified by SCX column, followed by silica gel flash column (DCM/MeOH/NH₄OH=90/10/1) to give 14B (9.5 mg, 17%). The compound has an analytical HPLC retention time=1.288 min

EXAMPLE 15

(3R,4R)-4-amino-1-((4-(3-methoxyphenylamino)
quinazolin-5-yl)methyl)-N-methylpiperidine-3-carboxamide

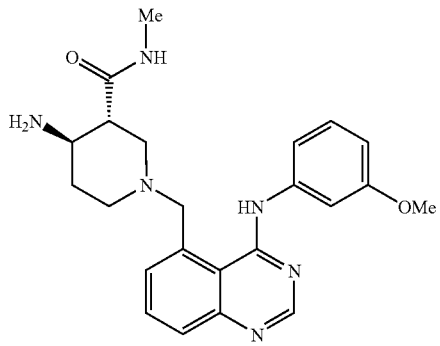

15A. Preparation of 5-(bromomethyl)-4-(methylthio)quinazoline

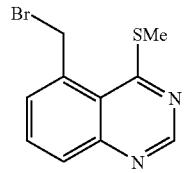

A mixture of 1B (5.0 g, 26.3 mmol), 2,2'-azobisisobutyronitrile (400 mg, 2.25 mmol) and N-bromosuccinimide (5.14 g, 31.3 mmol) in $CCl_4$ (60 ml) was degassed and purged with $N_2$, and heated to reflux under $N_2$ for 1 h. After cooling to room temperature, the reaction mixture was filtered through a pad of Celite. The filtrate was concentrated and the residue was triturated with $Et_2O$/hexane and dried to give 15A (4.9 g, 69%) as a solid. The compound has an analytical HPLC retention time=2.549 min (Chromolith SpeedROD column 4.6×50 mm, 10-90% aqueous methanol containing 0.1% TFA over 4 minutes, 4 mL/min, monitoring at 254 nm) and a LC/MS $M^++H=268^+$.

15B. Preparation of (3R,4R)-methyl 4-(allyloxycarbonyl)-1-((4-(methylthio)quinazolin-5-yl)methyl)piperidine-3-carboxylate

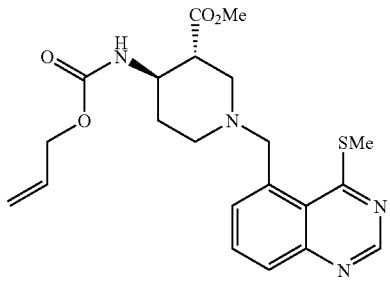

A mixture of 15A (2.02 g, 7.5 mmol), TFA salt of (3R,4R)-methyl 4-(allyloxycarbonyl)piperidine-3-carboxylate (2.8 g, 7.87 mmol), (prepared as described in U.S. patent application Ser. No. 11/019,901) and TEA (3.14 ml, 22.5 mmol) in dichloroethane (50 ml) was heated at 70° C. for 1 h. After cooling to room temperature, the reaction mixture was washed with water, dried and concentrated in vacuo. Purification using silica gel flash column (DCM/MeOH=98/

2) gave 15B (2.91 g, 90%) as a solid. The compound has an analytical HPLC retention time=1.547 min (Chromolith SpeedROD column 4.6×50 mm, 10-90% aqueous methanol containing 0.1% TFA over 4 minutes, 4 mL/min, monitoring at 254 nm) and a LC/MS $M^++H=431^+$.

15C. Preparation of (3R,4R)-methyl 4-(allyloxycarbonyl)-1-((4-(3-methoxyphenylamino)quinazolin-5-yl)methyl)piperidine-3-carboxylate

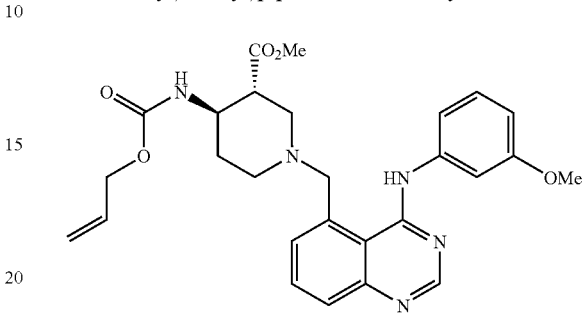

To a mixture of 15B (453 mg, 1.05 mmol), 3-methoxyaniline (142.5 mg, 1.16 mmol) in $CH_3CN$ (25 ml) was added $AgNO_3$ (197 mg, 1.16 mmol). The mixture was heated at 70° C. for 30 min. After cooling to room temperature, the solid was removed by filtration through a pad of Celite and the filtrate was concentrated in vacuo. The residue was taken into with water, treated with saturated $NaHCO_3$ and extracted with EtOAc (×3). The combined extracts were dried over anhydrous $Na_2SO_4$. Concentration in vacuo gave 644 mg of crude 15C as an oil, which was used in next step without further purification. The compound has an analytical HPLC retention time=2.259 min (Chromolith SpeedROD column 4.6×50 mm, 10-90% aqueous methanol containing 0.1% TFA over 4 minutes, 4 mL/min, monitoring at 254 nm) and a LC/MS $M^++H=506^+$.

15D. Preparation of (3R,4R)-4-(allyloxycarbonyl)-1-((4-(3-methoxyphenylamino)quinazolin-5-yl)methyl)piperidine-3-carboxylic acid

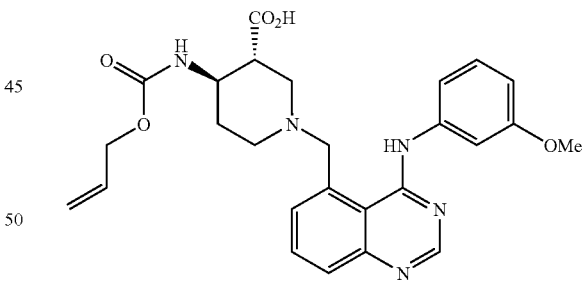

To a solution of 15C (644 mg, crude, maximum 1.05 mmol) in a mixture of MeOH/THF/$H_2O$ (6 ml/6 ml/3 ml) was added $LiOH.H_2O$ (466 mg, 11.1 mmol). The mixture was stirred at room temperature for 4 h and then concentrated. The residue was treated with saturated aqueous $NH_4Cl$ and extracted with a mixture of DCM/i-PrOH. The combined extracts were dried over $Na_2SO_4$, filtered, and concentrated in vacuo. The residue was purified by silica gel column (DCM/MeOH=9/1) to give 15D (360 mg, 70% overall from 15B). The compound has an analytical HPLC retention time=2.125 min (Chromolith SpeedROD column 4.6×50 mm, 10-90% aqueous methanol containing 0.1% TFA over 4 minutes, 4 mL/min, monitoring at 254 nm) and a LC/MS $M^++H=492^+$.

15E. Preparation of allyl(3R,4R)-1-((4-(3-methoxyphenylamino) quinazolin-5-yl)methyl)-3-(methylcarbamoyl)piperidin-4-ylcarbamate

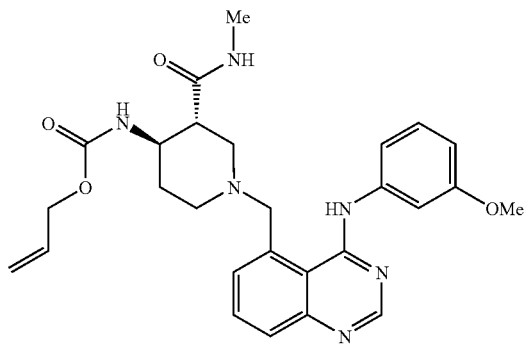

A suspension of 15D (98.2 mg, 0.2 mmol) in CH$_3$CN (2 ml) was treated with DIEA (35 μl, 0.2 mmol), Bop reagent (133 mg, 0.3 mmol) and 2N CH$_3$NH$_2$ in THF (0.3 ml, 0.6 mmol). The reaction was stirred at room temperature for 2.5 h and quenched with water. The mixture was purified by preparative HPLC and the desired fractions were combined and concentrated. After basifying with aq NaHCO$_3$ and extracted with EtOAc, the combined organic layers were dried and concentrated to give 15E (28.1 mg, 28%) as a solid. The compound has an analytical HPLC retention time=2.069 min (Chromolith SpeedROD column 4.6×50 mm, 10-90% aqueous methanol containing 0.1% TFA over 4 minutes, 4 mL/min, monitoring at 254 nm) and a LC/MS M$^+$+H=505$^+$.

15F. Preparation of (3R,4R)-4-amino-1-((4-(3-methoxyphenylamino) quinazolin-5-yl)methyl)-N-methylpiperidine-3-carboxamide A solution of 15E (27 mg, 0.054 mmol) in THF (3 ml) was degassed and purged with N$_2$. To this was added 2N Me$_2$NH in THF (95 μl, 0.19 mmol), followed by Pd(PPh$_3$)$_4$ (9 mg, 0.0078 mmol). The mixture was stirred at room temperature for 1.5 h. Concentration in vacuo followed by purification using preparative HPLC gave, after concentration and lyophilization, a TFA salt of 15F (20.3 mg, 70%) as a solid. The compound has an analytical HPLC retention time=1.307 min (Chromolith SpeedROD column 4.6×50 mm, 10-90% aqueous methanol containing 0.1% TFA over 4 minutes, 4 mL/min, monitoring at 254 nm) and a LC/MS M$^+$+H=421$^+$.

EXAMPLE 16

(3R,4R)-4-amino-1-((4-(3-methoxyphenylamino) quinazolin-5-yl)methyl)-N-(methylsulfonyl)piperidine-3-carboxamide

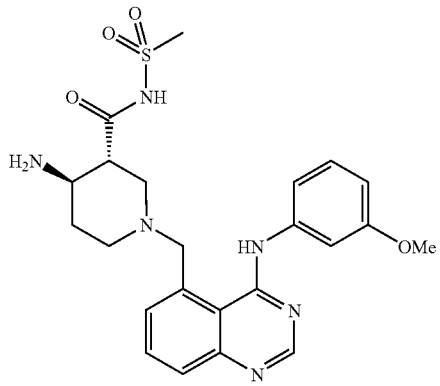

16A. Preparation of allyl(3R,4R)-1-((4-(3-methoxyphenylamino) quinazolin-5-yl)methyl)-3-(methylsulfonylcarbamoyl)piperidin-4-yl-carbamate

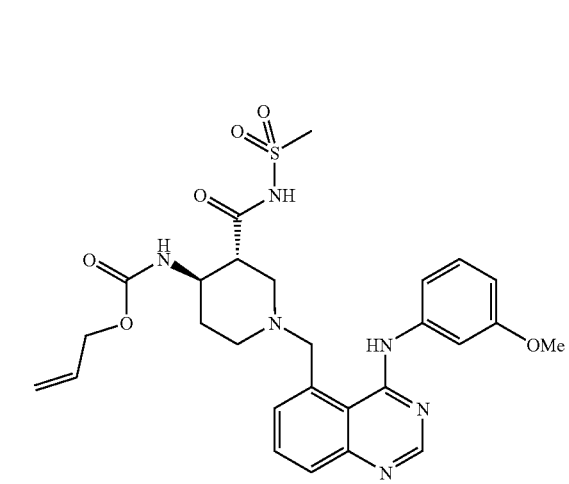

To a suspension of 15D (49 mg, 0.1 mmol) in CH$_3$CN (2.5 ml) was added DMAP (15 mg, 0.12 mmol), EDAC.HCl (27 mg, 0.14 mmol) and CH$_3$SO$_2$NH$_2$ (20 mg, 0.21 mmol). The reaction mixture was stirred at room temeprature overnight. After quenching with water, the reaction mixture was concentrated to dryness and the residue was purified by silica gel flash column (DCM/MeOH/NH4OH=95/5/0.5) to give 16A (30 mg, 53%). The compound has an analytical HPLC retention time=2.083 min (Chromolith SpeedROD column 4.6×50 mm, 10-90% aqueous methanol containing 0.1% TFA over 4 minutes, 4 mL/min, monitoring at 254 nm) and a LC/MS M$^+$+H=569$^+$.

16B. Preparation of (3R,4R)-4-amino-1-((4-(3-methoxyphenylamino) quinazolin-5-yl)methyl)-N-(methylsulfonyl)piperidine-3-carboxamide

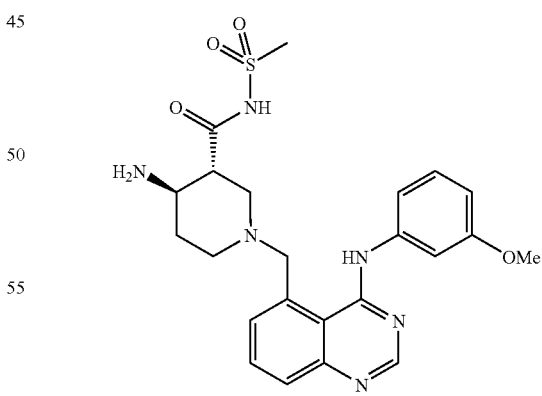

A TFA salt of 16B (16.4 mg, 52%) was prepared from 16A (30 mg, 0.053 mmol) using a similar procedure as described for 15F. The compound is a solid and has an analytical HPLC retention time=1.260 min (Chromolith SpeedROD column 4.6×50 mm, 10-90% aqueous methanol containing 0.1% TFA over 4 minutes, 4 mL/min, monitoring at 254 nm) and a LC/MS M$^+$+H=485$^+$.

EXAMPLE 17

((3R,4R)-4-Amino-1-((4-(3-methoxyphenylamino)quinazolin-5-yl)methyl)piperidin-3-yl)methanol

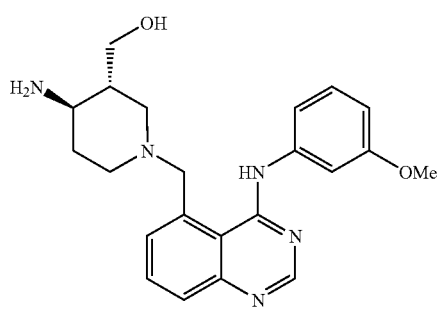

17A. Preparation of allyl(3R,4R)-3-(hydroxymethyl)-1-((4-(3-methoxyphenylamino)quinazolin-5-yl)methyl)piperidin-4-ylcarbamate

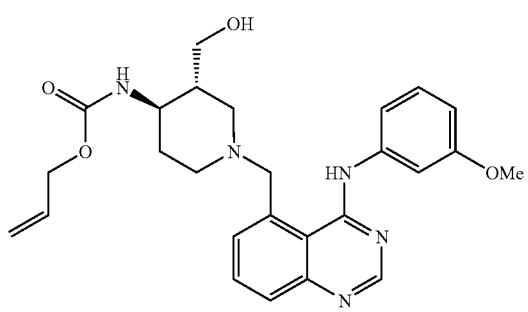

To a solution of 15D (112 mg, 0.228 mmol) in DCM (3 ml) was added pyridine (19 μl, 0.228 mmol), followed by cyanuric fluoride (62 μl, 0.684 mmol). The mixture was stirred at room temperature for 1 h. Ice water was added and the mixture was extracted with DCM (×2). The combined extracts were dried over anhydrous $Na_2SO_4$. The mixture was concentrated in vacuo and the residue was dissolved in DCM (3 ml). $NaBH_4$ (34 mg, 0.912 mmol) was added in one portion, followed by slow addition of MeOH (3 ml) over 30 min. The mixture was stirred at room temperature overnight. The mixture was concentrated in vacuo and the residue was treated with water and extracted with DCM. The combined extracts were dried, concentrated and purified by preparative HPLC. The desired fraction was combined and concentrated, basified with aq $NaHCO_3$ and extracted with EtOAc. The combined extracts were dried and concentrated to give 17A (22 mg, 20%) as a solid. The compound has an analytical HPLC retention time=2.117 min (Chromolith SpeedROD column 4.6×50 mm, 10-90% aqueous methanol containing 0.1% TFA over 4 minutes, 4 mL/min, monitoring at 254 nm) and a LC/MS $M^++H=478^+$.

17B. Preparation of ((3R,4R)-4-amino-1-((4-(3-methoxyphenylamino) quinazolin-5-yl)methyl)piperidin-3-yl)methanol

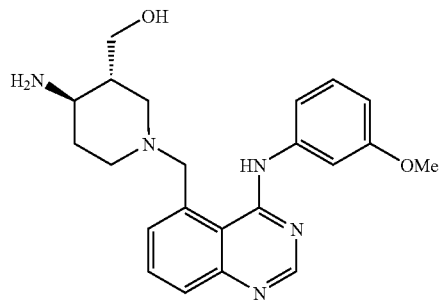

A TFA salt of compound 17B (9.6 mg, 41%) was prepared from 17A (22 mg, 0.046 mmol) using a similar procedure as described for 15F. The salt is a solid and has an analytical HPLC retention time=1.266 min (Chromolith SpeedROD column 4.6×50 mm, 10-90% aqueous methanol containing 0.1% TFA over 4 minutes, 4 mL/min, monitoring at 254 nm) and a LC/MS $M^++H=394^+$.

EXAMPLE 18

((3R,4R)-4-amino-1-((4-(3-ethynylphenylamino)quinazolin-5-yl)methyl)piperidin-3-yl)methanol

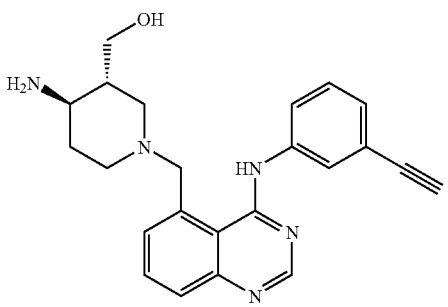

18A. Preparation of (3R,4R)-methyl 4-(allyloxycarbonyl)-1-((4-(3-ethynylphenylamino)quinazolin-5-yl)methyl)piperidine-3-carboxylate

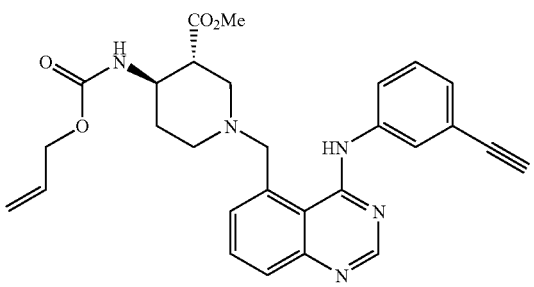

Compound 18A was prepared from 15B and 3-ethynylaniline in a similar way as 15C. It has an analytical HPLC retention time=2.353 min (Chromolith SpeedROD column 4.6×50 mm, 10-90% aqueous methanol containing 0.1% TFA over 4 minutes, 4 mL/min, monitoring at 254 nm) and a LC/MS $M^++H=500^+$.

18B. Preparation of (3R,4R)-methyl 4-amino-1-((4-(3-ethynylphenylamino)quinazolin-5-yl)methyl)piperidine-3-carboxylate

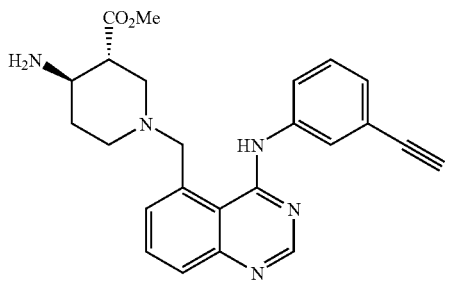

Compound 18B was prepared from 18A in a similar way as 15F. It has an analytical HPLC retention time=1.546 min (Chromolith SpeedROD column 4.6×50 mm, 10-90% aqueous methanol containing 0.1% TFA over 4 minutes, 4 mL/min, monitoring at 254 nm) and a LC/MS $M^+ + H = 416^+$.

18C. Preparation of ((3R,4R)-4-amino-1-((4-(3-ethynylphenylamino)quinazolin-5-yl)methyl)piperidin-3-yl)methanol

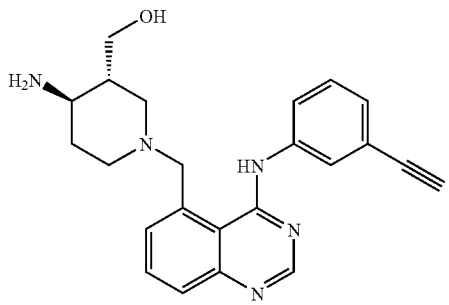

To a solution of 18B (41.5 mg, 0.1 mmol) in THF (2 ml) was added 1.0M LiAlH4 in THF (0.3 ml, 0.3 mmol) at −78° C. The mixture was stirred at −78° C. for 1 h, then at RT for 30 min. The reaction was quenched with MeOH while being cooled. The resulting mixture was filtered through Celite, the filtrate was concentrated and purified by prep HPLC, and the desired fraction was lyophilized to give a TFA salt of 18C (19.0 mg, 38%) as a solid. It has an analytical HPLC retention time=1.404 min (Chromolith SpeedROD column 4.6×50 mm, 10-90% aqueous methanol containing 0.1% TFA over 4 minutes, 4 mL/min, monitoring at 254 nm) and a LC/MS $M^+ + H = 388^+$.

EXAMPLE 19

(3R,4R)-1-((4-(1-(3-fluorobenzyl)-1H-indazole-5-ylamino)quinazolin-5-yl)methyl)-4-aminopiperidin-3-ol

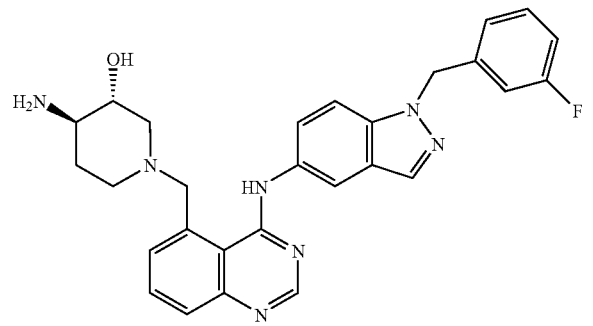

19A. Preparation of (3R,4R)-1-((4-(1-(3-fluorobenzyl)-1H-indazol-5-ylamino)quinazolin-5-yl)methyl)-4-azidopiperidin-3-ol

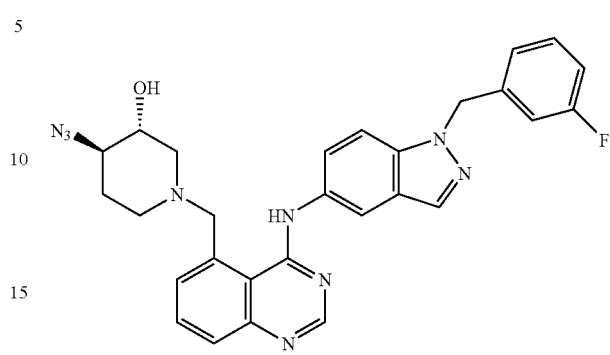

A mixture of 14A (120 mg, 0.34 mmol) and 1-(3-fluorobenzyl)-1H-indazole-5-amine (81.0 mg, 0.34 mmol; prepared as described in US 2003/0186983 A1) in $CH_3CN$ (1.2 ml) was heated at 55° C. for 45 min. After cooled to rt, (3R,4R)-4-azidopiperidin-3-ol (475 mg, 3.34 mmol; prepared as described in U.S. patent application Ser. No. 10146 PSP) was added and the mixture was heated at 60° C. for 16 h. This mixture was diluted with CH3CN (2.4 mL), and then heated at 70° C. for 4 h and at 80° C. for 4 d. The reaction mixture was concentrated in vacuo and the residue was purified by prep HPLC. to give 19A (78 mg, 45%). It has an analytical HPLC retention time=2.43 min (Chromolith SpeedROD column 4.6×50 mm, 10-90% aqueous methanol containing 0.2% $H_3PO_4$ over 4 minutes, 4 mL/min, monitoring at 220 nm) and a LC/MS $M^+ + H = 524^+$.

19B. Preparation of (3R,4R)-1-((4-(1-(3-fluorobenzyl)-1H-indazole-5-ylamino)quinazolin-5-yl)methyl)-4-aminopiperidin-3-ol

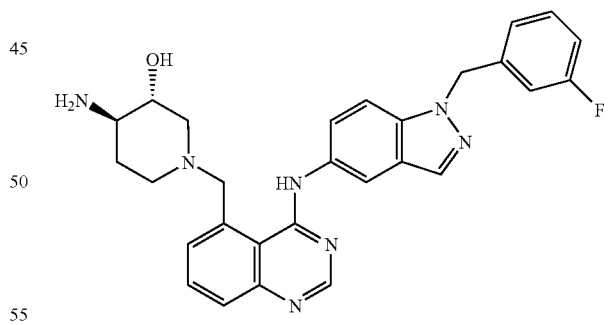

19A (78.0 mg, 0.15 mmol) was dissolved in a mixture of $THF/H_2O$ (1.2 ml/0.2 ml) and $PPh_3$ (60.0 mg, 0.23 mmol) was added. The mixture was heated at 70° C. for 2 h. After cooled to rt, the reaction mixture was concentrated in vacuo and purified by prep HPLC to give 19B (85.0 mg, 93%) as a TFA salt. It has an analytical HPLC retention time=1.84 min (Chromolith SpeedROD column 4.6×50 mm, 10-90% aqueous methanol containing 0.1% TFA over 4 minutes, 4 mL/min, monitoring at 254 nm) and a LC/MS $M^+ + H = 498^+$.

EXAMPLE 20

(3R,4R)-1-((4-(4-(3-fluorobenzyloxy)-3-chlorophenylamino)quinazolin-5-yl)methyl)-4-aminopiperidin-3-ol

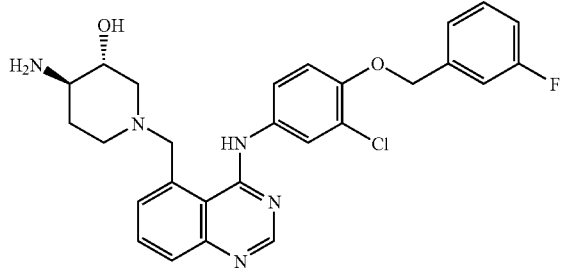

20A. Preparation of (3R,4R)-1-((4-(4-(3-fluorobenzyloxy)-3-chlorophenylamino)quinazolin-5-yl)methyl)-4-aminopiperidin-3-ol

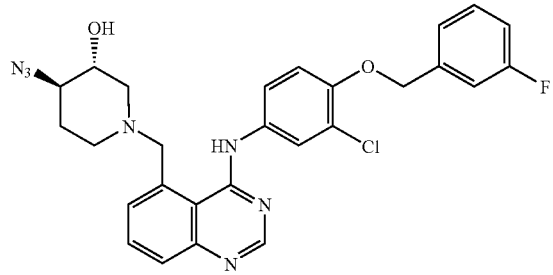

The preparation was carried out from 14A (120 mg) and 4-(3-fluorobenzyloxy)-3-chlorobenzenamine (84 mg, prepared as described in U.S. Ser. No. 11/019,899 filed Dec. 22, 2004) in a similar way as described in example 19A in 17% yield. It has an analytical HPLC retention time=2.91 min (Chromolith SpeedROD column 4.6×50 mm, 10-90% aqueous methanol containing 0.2% $H_3PO_4$ over 4 minutes, 4 mL/min, monitoring at 220 nm) and a LC/MS $M^++H=534^+$.

20B. Preparation of (3R,4R)-1-((4-(4-(3-fluorobenzyloxy)-3-chlorophenylamino)quinazolin-5-yl)methyl)-4-aminopiperidin-3-ol

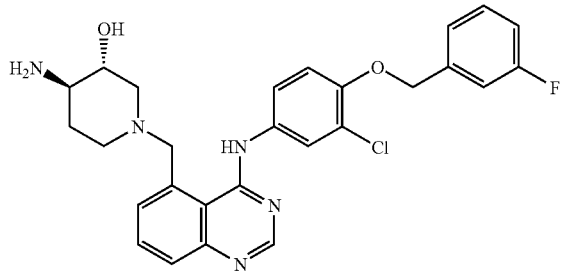

The preparation was carried out from 20A (14 mg) in a similar way as described in example 19B in 81% yield. It has an analytical HPLC retention time=2.34 min (Chromolith SpeedROD column 4.6×50 mm, 10-90% aqueous methanol containing 0.1% TFA over 4 minutes, 4 mL/min, monitoring at 254 nm) and a LC/MS $M^++H=508^+$.

EXAMPLE 21

N-(1-(3-fluorobenzyl)-1H-indazol-5-yl)-5-((4-aminopiperidin-1-yl)methyl)quinazolin-4-amine

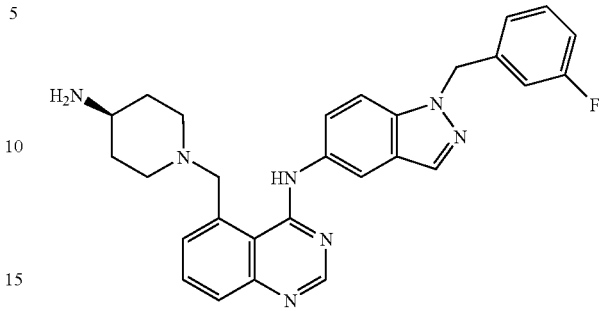

21A. Preparation of tert-butyl 1-((4-(1-(3-fluorobenzyl)-1H-indazol-5-ylamino)quinazolin-5-yl)methyl)piperidin-4-ylcarbamate

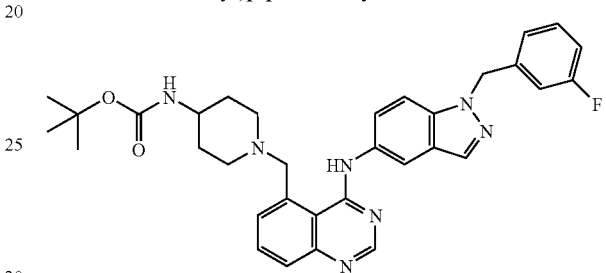

A mixture of 14A (120 mg, 0.34 mmol) and 1-(3-fluorobenzyl)-1H-indazole-5-amine (81.0 mg, 0.34 mmol; prepared as described in US 2003/0186983 A1) in $CH_3CN$ (1.2 ml) was heated at 55° C. for 45 min. After cooling to rt, tert-butyl piperidin-4-ylcarbamate (672 mg, 3.34 mmol) was added and the mixture was heated at 60° C. for 16 h. After cooling to rt. this mixture was then diluted with $CH_3CN$ (2.4 mL), and heated at 70° C. for 4 h and at 80° C. for 4 d. The reaction mixture was concentrated in vacuo and the residue was purified by prep HPLC to give 21A (52 mg, 27%). It has an analytical HPLC retention time=2.86 min (Chromolith SpeedROD column 4.6×50 mm, 10-90% aqueous methanol containing 0.2% $H_3PO_4$ over 4 minutes, 4 mL/min, monitoring at 220 nm) and a LC/MS $M^++H=582^+$.

21B. Preparation of N-(1-(3-fluorobenzyl)-1H-indazol-5-yl)-5-((4-aminopiperidin-1-yl)methyl)quinazolin-4-amine

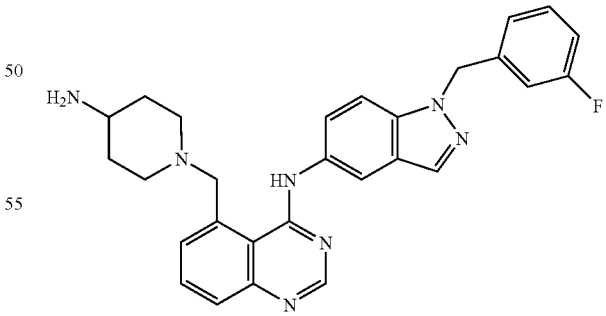

21A (52 mg, 0.089 mmoL) was dissolved in a mixture of TFA/DCM (2 ml/2 ml) and stirred at rt for 10 min, then concentrated. The residue was purified by prep HPLC to give 21B (38 mg, 88%). It has an analytical HPLC retention time=1.93 min (Chromolith SpeedROD column 4.6×50 mm, 10-90% aqueous methanol containing 0.1% TFA over 4 minutes, 4 mL/min, monitoring at 254 nm) and a LC/MS $M^++H=482^+$.

EXAMPLE 22

N-(4-(3-fluorobenzyloxy)-3-chlorophenyl)-5-((4-aminopiperidin-1-yl)methyl)quinazolin-4-amine

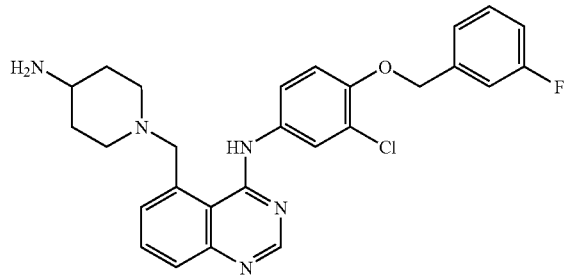

22A. Preparation of tert-butyl 1-((4-(4-(3-fluorobenzyloxy)-3-chlorophenylamino)quinazolin-5-yl)methyl)piperidin-4-ylcarbamate

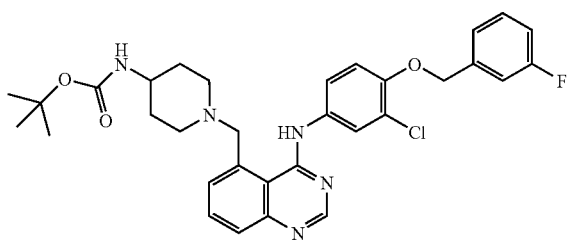

The preparation was carried out from 14A (120 mg) and 4-(3-fluorobenzyloxy)-3-chlorobenzenamine (84 mg, prepared as described in U.S. patent application Ser. No. 11/019,899 filed Dec. 22, 2004) in a similar way as described in example 22A in 34% yield. It has an analytical HPLC retention time=3.28 min (Chromolith SpeedROD column 4.6×50 mm, 10-90% aqueous methanol containing 0.2% $H_3PO_4$ over 4 minutes, 4 mL/min, monitoring at 220 nm) and a LC/MS $M^++H=592^+$.

22B. Preparation of N-(4-(3-fluorobenzyloxy)-3-chlorophenyl)-5-((4-aminopiperidin-1-yl)methyl)quinazolin-4-amine

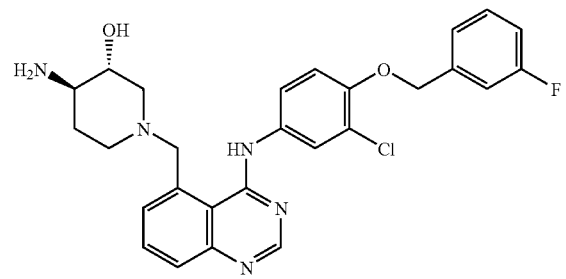

The preparation was carried out from 20A (68 mg) in a similar way as described in example 21B in 81% yield. It has an analytical HPLC retention time=2.40 min (Chromolith SpeedROD column 4.6×50 mm, 10-90% aqueous methanol containing 0.1% TFA over 4 minutes, 4 mL/min, monitoring at 254 nm) and a LC/MS $M^++H=492^+$.

EXAMPLE 23

(3R,4R)-4-amino-1-((4-(3-methoxyphenylamino)quinazolin-5-yl)methyl)-3-piperidinol

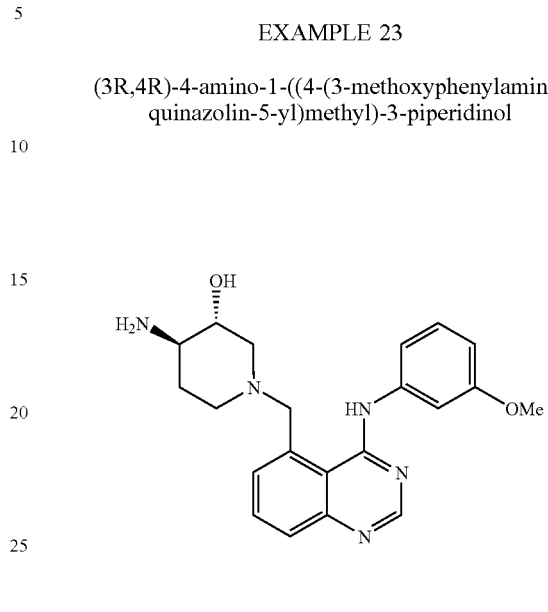

Compound 23 was prepared according to a procedure similar to that used for Ex. 14. The HPLC Rt=1.20 min; MS: 380+(M+H)+.

We claim:

1. A compound selected from the group consisting of
   (3R,4R)-4-amino-1-((4-(3-methoxyphenylamino)quinazolin-5-yl)methyl)-N-methylpiperidine-3-carboxamide,
   (3R,4R)-4-amino-1-[[4-[(3-ethynylphenyl)amino]-5-quinazolinyl]methyl]-3-piperidinol,
   N-(4-(3-fluorobenzyloxy)-3-chlorophenyl)-5-((4-aminopiperidin-1-yl)methyl)quinazolin-4-amine,
   (3R,4R)-1-((4-(1-(3-fluorobenzyl)-1H-indazole-5-ylamino)quinazolin-5-yl)methyl)-4-aminopiperidin-3-ol,
   ((3R,4R)-4-amino-1-((4-(3-ethynylphenylamino)quinazolin-5-yl)methyl)piperidin-3-yl)methanol,
   or a pharmaceutically acceptable salt thereof.

2. A pharmaceutical composition comprising one or more compounds of claim 1 and a pharmaceutically acceptable carrier.

* * * * *